(12) United States Patent
Ichizawa et al.

(10) Patent No.: US 9,170,194 B2
(45) Date of Patent: Oct. 27, 2015

(54) MATERIAL PROPERTY MEASURING APPARATUS

(71) Applicant: YOKOGAWA ELECTRIC CORPORATION, Musashino-shi, Tokyo (JP)

(72) Inventors: Yasushi Ichizawa, Musashino (JP); Kumiko Horikoshi, Musashino (JP); Kazuki Setsuda, Musashino (JP); Naomichi Chida, Musashino (JP)

(73) Assignee: YOKOGAWA ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 14/388,298

(22) PCT Filed: Mar. 28, 2013

(86) PCT No.: PCT/JP2013/059298
§ 371 (c)(1),
(2) Date: Sep. 26, 2014

(87) PCT Pub. No.: WO2013/147038
PCT Pub. Date: Oct. 3, 2013

(65) Prior Publication Data
US 2015/0090885 A1   Apr. 2, 2015

(30) Foreign Application Priority Data
Mar. 28, 2012 (JP) .................................. 2012-073652

(51) Int. Cl.
*G01N 21/3559* (2014.01)
*G01N 21/59* (2006.01)
*G01N 21/86* (2006.01)
(Continued)

(52) U.S. Cl.
CPC ............ *G01N 21/3559* (2013.01); *G01N 21/59* (2013.01); *G01N 21/86* (2013.01);
(Continued)

(58) Field of Classification Search
CPC .......... G01J 5/20; G01J 5/02; G01N 21/3559; G01N 21/59; G01N 21/86; G01N 2021/8663
USPC ........................................................ 250/349
See application file for complete search history.

(56) References Cited

U.S. PATENT DOCUMENTS 4,804,849 A * 2/1989 Booth et al. ................. 250/459.1
5,303,165 A * 4/1994 Ganz et al. ..................... 356/319
(Continued)

FOREIGN PATENT DOCUMENTS

JP   5-87733 A   4/1993
JP   5-118994 A   5/1993
(Continued)

OTHER PUBLICATIONS

International Search Report dated Jun. 18, 2013 issued in International Application No. PCT/JP2013/059298 (PCT/ISA/210).
(Continued)

*Primary Examiner* — David Porta
*Assistant Examiner* — Faye Boosalis
(74) *Attorney, Agent, or Firm* — Sughrue Mion, PLLC

(57) ABSTRACT

A material property measuring apparatus includes a radiation source irradiator configured to irradiate a measurement target material with radiation beams having n different wavelengths, a detector configured to detect intensities of radiation beams having the respective wavelengths after the irradiation of the measurement target material, and a processing unit configured to correct the detected intensity of the radiation beam having at least a part of the respective wavelengths using a correction coefficient in which rows and columns are respectively represented by a matrix of an order of n or less, and to calculate an index value indicating a property of the measurement target material on the basis of relative intensities of the radiation beams having the respective wavelengths after the correction.

12 Claims, 7 Drawing Sheets

(51) Int. Cl.
 *G01J 5/02* (2006.01)
 *G01N 21/31* (2006.01)
(52) U.S. Cl.
 CPC *G01N2021/3148* (2013.01); *G01N 2021/3174* (2013.01); *G01N 2021/3181* (2013.01); *G01N 2021/8663* (2013.01); *G01N 2201/0627* (2013.01)

(56) References Cited

U.S. PATENT DOCUMENTS 5,719,665 A * 2/1998 Yamazoe ........................ 356/70
7,256,892 B2 * 8/2007 Nakajima ..................... 356/417
2006/0108540 A1 5/2006 Nakajima
2012/0019815 A1 1/2012 Horikoshi et al.

FOREIGN PATENT DOCUMENTS

JP 2004-163312 A 6/2004
JP 2012-26746 A 2/2012

OTHER PUBLICATIONS

Written Opinion dated Jun. 18, 2013 issued in International Application No. PCT/JP2013/059298 (PCT/ISA/237).

* cited by examiner

MATERIAL PROPERTY MEASURING APPARATUS

TECHNICAL FIELD

The present invention relates to a material property measuring apparatus which irradiates a measurement target material with radiation beams having different wavelengths and measures a property of the measurement target material on the basis of relative intensities of radiation beams having the respective wavelengths after the irradiation of the measurement target material. In particular, the present invention relates to a material property measuring apparatus capable of performing a high-accuracy measurement even without using radiation beams each having a spectrum which has an extremely narrow half-value width.

BACKGROUND ART

In a paper making process of manufacturing paper continuously, it is important to control the water content. This necessitates a water content measuring apparatus for measuring, online, the water content of paper that is being moved in a paper making line. Among several types of water content measuring apparatus that have been put into practice, an infrared water content measuring apparatus using near infrared light is used widely as an online water content measuring apparatus.

In infrared water content measuring apparatus, radiation having such a wavelength as to be absorbed by water and not to be absorbed by cellulose which is the main component of paper and radiation having such a wavelength as to be absorbed by cellulose and not to be absorbed by water are caused to pass through a paper as a measurement target. A water content of the paper is calculated on the basis of an intensity ratio between radiation beams having the respective wavelengths measured by a radiation receiver. Reference radiation having such a wavelength as to be absorbed by neither water nor cellulose may also be used to eliminate influences of radiation scattering by the paper, substances mixed in the paper, the basis weight, the ash content, the lignin content, colorants used, a coating, and other factors.

FIG. 6 is a block diagram showing the configuration of a related-art infrared water content measuring apparatus 40. As shown in FIG. 6, in the related-art infrared water content measuring apparatus 40, a halogen lamp 410 having a broad, continuous spectrum is generally used as a radiation source. Radiation emitted from the halogen lamp 410 is guided, via a projection lens 411, to band-pass filters 421 which are mounted on a filter wheel 420.

In the example of FIG. 6, three kinds of band-pass filters, that is, a band-pass filter 421a which transmits reference radiation having such a wavelength $\lambda_a$ as to be absorbed by neither water nor cellulose, a band-pass filter 421b which transmits radiation having such a wavelength $\lambda_b$ as to absorbed by water and not to absorbed by cellulose, and a band-pass filter 421c which transmits radiation having such a wavelength $\lambda_c$ as to absorbed by cellulose and not to absorbed by water, are mounted on the filter wheel 420. However, there are other cases in which four or more band-pass filter 421 are used to produce plural reference radiation beams having different wavelengths.

Radiation beams having the respective wavelengths are output sequentially in accordance with rotation of the filter wheel 420. It is assumed that, as shown in a broken-like rectangle A, the radiation beam having the wavelength $\lambda_a$ is output at time point $t_1$, the radiation beam having the wavelength $\lambda_b$ is output at time point $t_2$ and the radiation beam having the wavelength $\lambda_c$ is output at time point $t_3$. To prevent reduction of measurement accuracy due to inclusion of components having other wavelengths, each band-pass filter 421 is required to have a specification in which a half-value width of a spectrum of the output radiation beams is an extremely narrow.

Radiation that has passed through the band-pass filter 421 is applied onto paper 700 as a measurement target. To increase the sensitivity, the infrared water content measuring apparatus 40 is configured in such a manner that the paper 700 is interposed between a top reflector 431 having an entrance hole and a bottom reflector 432 having an exit hole so that radiation passes through, many times, the paper 700 which is moving in a paper making line.

Radiation that is output through the exit hole of the bottom reflector 432 is detected by a radiation receiver 440 such as a PbS cell and a resulting detection signal is amplified by an amplifier 441. As shown in a broken-line rectangle B, amplified detection signals are obtained in time-series at time points corresponding to time points of output of radiation beams from the respective band-pass filters 421. More specifically, a signal $V_a$ which is obtained at time point $t_1$ corresponds to intensity of the radiation beam having the wavelength $\lambda_a$, a signal $V_b$ which is obtained at time point $t_2$ corresponds to intensity of the radiation beam having the wavelength $\lambda_b$, and a signal $V_c$ which is obtained at time point $t_3$ corresponds to intensity of the radiation beam having the wavelength $\lambda_c$.

The amplified detection signals are input to a processing unit 450, where an index value calculator 451 calculates an index value on the basis of an intensity ratio between the detection signals corresponding to the respective wavelengths. Then, a water content calculator 452 converts the index value into a water content by referring to a calibration curve 453 which was prepared in advance, and outputs information of the water content. The calibration curve 453 is data which correlates correct water contents measured by an electronic balance or the like with index values measured by the infrared water content measuring apparatus 40.

PRIOR ART DOCUMENTS

Patent Documents

[Patent document 1] JP-A-5-118984

SUMMARY OF INVENTION

Technical Problem

As described above, in the infrared water content measuring apparatus 40, a water content is measured by measuring transmission intensities of reference radiation having such a wavelength $\lambda_a$ as to be absorbed by neither water nor cellulose, radiation having such a wavelength $\lambda_b$ as to absorbed by water and not to absorbed by cellulose, and radiation having such a wavelength $\lambda_c$ as to absorbed by cellulose and not to absorbed by water.

FIG. 7 is a graph showing absorption characteristics at each wavelength in a case of a paper with a water content of 5% and in a case of the same paper with a water content of 15%. The horizontal axis represents the wavelength and the vertical axis represents the transmission intensity. It is an ideal characteristic that the two curves have a difference $D_b$ due to a water content difference only at the wavelength $\lambda_b$ at which radiation is absorbed only by water. However, actually, the two curves also have differences $D_a$ and $D_c$ at the respective wavelengths $\lambda_a$ and $\lambda_c$, which means that radiation beams having the respective wavelengths $\lambda_a$ and $\lambda_c$ are also affected by water.

As a result, non-negligible error may occur if an index value is calculated using a measured intensity ratio without any change and then converted into a water content.

Furthermore, it is known that the spectrum of each of radiation beams used for a measurement has a broad half-value width, other wavelength components included in each radiation beam and a degree of variation in the calibration curve increases depending on paper type. Since it is not realistic to prepare calibration curves for respective paper types (products), a related-art measure is to use band-pass filters 421 each having a spectrum with an extremely narrow half-value width to prevent reduction in measurement accuracy due to a paper-type-dependent variation of the calibration curve. However, such band-pass filters 421 cause high degrees of radiation attenuation. Therefore, to enable measurement of thick paper, it is necessary to use a high-power halogen lamp 410, resulting in increase in the size and price of the apparatus because of employment of a cooling mechanism, a power source, etc. that are suitable for it.

If a high-accuracy measurement could be performed using radiation beams each having a spectrum with a broad half-value width, it would be possible to use LEDs (light-emitting diodes) as radiation sources for the respective wavelengths. Although spectrum of LEDs have broad half-value widths, they are advantages over halogen lamps in many respects such as easiness of maintenance, life, power consumption, and price. The use of LEDs which emit radiation at necessary wavelengths would make it possible to omit the band-pass filters 421 and to thereby eliminate wear and failure risk of mechanical, moving parts as used in the filter wheel 420.

Furthermore, if a high-accuracy measurement could be performed using radiation beams each having a spectrum with a broad half-value width, the specification in relation to the half-value-width required for each band-pass filter 421 would be relaxed even in the case where the halogen lamp 410 is used as a radiation source. Therefore, the degree of radiation attenuation would be lowered and hence increase in the size and price of the apparatus would be prevented.

Thus, an object of the present invention is to perform a high-accuracy measurement even without using radiation beams each having a spectrum which has an extremely narrow half-value width, by a material property measuring apparatus which irradiates a measurement target material with radiation beams having different wavelengths and measures a property of the measurement target material on the basis of relative intensities of radiation beams having the respective wavelengths after the irradiation of the measurement target material.

Solution to Problem

In order to solve the problem, a material property measuring apparatus according to the present invention, comprises a radiation source irradiator configured to irradiate a measurement target material with radiation beams having n different wavelengths, a detector configured to detect intensities of radiation beams having the respective wavelengths after the irradiation of the measurement target material, and a processing unit configured to correct the detected intensities of the radiation beams having the respective wavelengths using a correction coefficient which is represented by a square matrix of an order of n, and to calculate an index value indicating a property of the measurement target material on the basis of relative intensities of the radiation beams having the respective wavelengths after the correction.

Here, the processing unit can convert the calculated index value into a property value by referring to a calibration curve which correlates the index value with the property value, after the calculation of the index value, and the correction coefficient can be determined so that the degree of coincidence between calibration curves for a plurality of kinds of the measurement target material satisfies a certain criterion.

Further, the radiation source irradiator can comprise n LEDs (Light Emitting Diodes) which emit radiation beams having the respective wavelengths, respectively.

In this case, the radiation source irradiator can drive the n LEDs while modulating them at different frequencies, and the detector can comprise a frequency discriminator configured to detect a signal having a particular frequency from a frequency-modulated signal.

Further, the radiation source irradiator can reflect and diffuse the radiation beams emitted from the n LEDs and irradiate the measurement target material with the radiation beams simultaneously.

In each case, the measurement target material is paper, the property is a water content, and the radiation beams having the n different wavelengths has three or more wavelengths, and can include a radiation beam having such a wavelength as to be absorbed by water, a radiation beam having such a wavelength as to be absorbed by cellulose, and a radiation beam having such a wavelength as not to tend to be absorbed by water or cellulose.

Effect of Invention

According to the present invention, it is possible to perform a high-accuracy measurement even without using radiation beams each having a spectrum which has an extremely narrow half-value width, by the material property measuring apparatus which irradiates a measurement target material with radiation beams having different wavelengths and measures a property of the measurement target material on the basis of relative intensities of radiation beams having the respective wavelengths after the irradiation of the measurement target material.

DESCRIPTION OF EMBODIMENTS

An embodiment of the present invention will be hereinafter described with reference to the drawings. In the embodiment, a material property measuring apparatus according to the invention is applied to an infrared water content measuring apparatus for measuring a water content of paper using infrared light.

Figure 1:
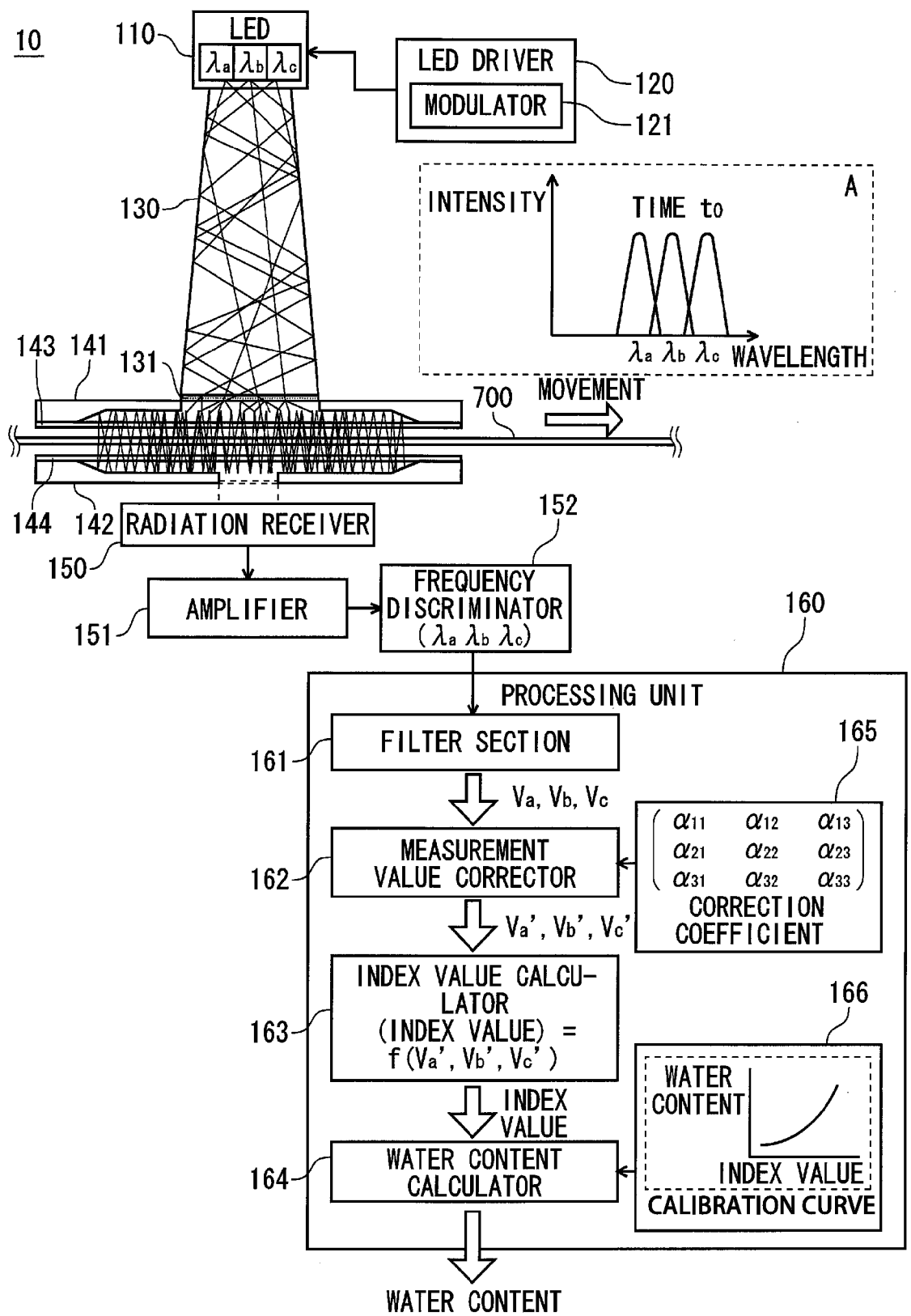
FIG. 1 is a block diagram showing the configuration of an infrared water content measuring apparatus according to an embodiment.

FIG. 1 is a block diagram showing the configuration of an infrared water content measuring apparatus 10 according to the embodiment. As shown in FIG. 1, the infrared water content measuring apparatus 10 employs, as a radiation source, an LED unit 110 incorporating three LEDs which emit radiation at respective wavelengths $\lambda_a$, $\lambda_b$, and $\lambda_c$. It is desirable that the LED unit 110 has a cooling function. In the embodiment, since the LEDs are employed as the radiation source, the radiation source and the cooling device can be miniaturized. In online measuring apparatus, in general, the miniaturization of the apparatus is effective because plural sensors are incorporated together in a measurement head.

The wavelength $\lambda_a$ is a wavelength at which radiation is absorbed by neither water nor cellulose, and may be set at about 1.7 μm, for example. The wavelength $\lambda_b$ is a wavelength at which radiation is absorbed by water and not by cellulose, and may be set at about 1.9 μm, for example. The wavelength $\lambda_c$ is a wavelength at which radiation is absorbed by cellulose and not by water, and may be set at about 2.1 μm, for example.

The LEDs incorporated in the LED unit 110 are driven by an LED driver 120 to emit radiation. Since the LEDs can be modulated electrically, the LED driver 120 is equipped with a modulator 121 and the LEDs are caused to emit radiation while being modulated at different frequencies. The modulation frequencies may be set at several kilohertz, for example. The reason for modulating the LEDs is to detect signals in a frequency band with small noise. Modulating the LEDs makes themselves less prone to be affected by near infrared light that is emitted from paper 700 being in a high-temperature state during an online measurement, whereby increase in measurement accuracy is expected.

As shown in a broken-line rectangle A of FIG. 1, radiation beams emitted from the LED unit 110 are broader in half-value width than radiation beams that are made to pass through related-art band-pass filters. However, since a filter wheel is not used, it is possible to emit radiation beams simultaneously at time $t_0$ and apply them to paper 700 simultaneously. Therefore, even while paper 700 is moving in a paper making line, a measurement can be performed by applying radiation beams having the respective wavelengths to its same portion. It is expected that this reduces measurement unevenness, because in the related art, radiation beams having the respective wavelengths are applied sequentially to different portions of paper 700. Furthermore, since a filter wheel having mechanical, moving portions is not employed, the apparatus can not only be miniaturized but also made free of wear and failure risk. The apparatus is thus increased in reliability, durability, and ease of maintenance.

Radiation beams having the respective wavelengths as emitted from the LED unit 110 have disorder in spatial uniformity because they are emitted from different positions. As a countermeasure, a polygonal tube reflector 130 having inner surfaces that are covered with a high-reflectance reflective material is disposed right next to the LED unit 110. A light pipe may be used in place of the tube reflector 130. It is preferable that the tube reflector 130 or the light pipe be shaped like a prism or a pyramid that becomes wider toward the exit. With this measure, radiation beams having the respective wavelengths are mixed together properly and resulting radiation that is high in spatial uniformity can be guided to paper 700 as a measurement target with high efficiency.

In the example of FIG. 1, to enhance the above effect, a diffusion sheet 131 is disposed close to the exit of the tube reflector 130. However, depending on the features of a measurement target material such as thickness of a paper, the diffusion sheet 131 may be omitted or its diffusion intensity may be adjusted.

A thin top reflector 141 having an entrance hole is disposed downstream of the tube reflector 130 in such a manner that its reflection surface is located on the side of the paper 700 as a measurement target material. A bottom reflector 142 having approximately the same shape as the top reflector 141 and having an exit hole is opposed to the top reflector 141 in such a manner that they optical axes are aligned with each other. To prevent entrance of paper powder or water, thin glass windows 143 and 144 are bonded to the respective reflectors 141 and 142 on the sides of the measurement target material. The above-described blocks function as a radiation source irradiator.

Radiation that is output through the exit hole of the bottom reflector 142 is detected by a radiation receiver 150 such as a photodiode which has high sensitivity at the three wavelengths so as to produce a waveform which is a superimposition of signals corresponding to the three respective wavelengths. The detection signal is amplified by an amplifier 151 first, and input to a frequency discriminator 152. The amplifier 151 and the frequency discriminator 152 function as a detector.

The frequency discriminator 152, which is a device for detecting an original signal wave from a frequency-modulated signal, enables detection of a very small signal buried in noise and signal detection with very high sensitivity by detecting the signals at the frequency band with small noise. The use of the frequency discriminators 152 increases the measurement accuracy of paper having a large basis weight. In the embodiment, since the LEDs are driven being frequency-modulated, signals corresponding to the respective wavelengths can be detected with high accuracy using the frequency discriminator 152.

The frequency discriminator 152 may be a known one, and for example, it is possible to use a scheme of extracting a frequency component of a detection target by using an FFT or a lock-in amplifier which detects and amplifies a signal having a particular frequency. In this case, a 2-phase configuration is employed which does not require phase adjustment. That is, an input signal is detected as an X component and a Y component by multiplying it by signals having a 90° phase difference with two multipliers. Then, amplitude values of the input signal are obtained through a vector calculation. The amplitude values are multiplied by the modulation signal that was used by the modulator 121, whereby amplitude values of the signal as the detection target are converted into a DC signal. A signal corresponding to the wavelength concerned can be detected by eliminating unnecessary components using a lowpass filter. The above-described circuit elements are provided in three sets. The detected signals corresponding to intensities of the radiation beams having the respective wavelengths are adjusted in gain and then output. It is desirable that a measurement with radiation irradiation and detection of signals corresponding to intensities of the radiation beams having the respective wavelengths be performed plural times.

The output of the frequency discriminator 152 is input to a processing unit 160. As shown in FIG. 1, the processing unit 160 has a filter section 161, a measurement value corrector 162, an index value calculator 163, and a water content calculator 164.

To reduce a variation of the measurement result, the filter section 161 averages the detected signals corresponding to intensities of the radiation beams having the respective wavelengths based on moving averaging, for example.

The measurement value corrector 162 corrects the values of the signals corresponding to intensities of the radiation beams having the respective wavelengths using a correction coefficient 165. Where the number of wavelengths is three, the correction coefficient 165 can be represented by a square matrix of 3×3. The measurement value corrector 162 corrects the values ($V_a$, $V_b$, $V_c$) corresponding to intensities of the radiation beams having the respective wavelengths into corrected values ($V_a'$, $V_b'$, $V_c'$) according to Formula 1, whereby mutual influences between the radiation beams having the respective wavelengths can be corrected for. A procedure for determining the correction coefficient 165 will be described later.

$$\begin{pmatrix} V_a' \\ V_b' \\ V_c' \end{pmatrix} = \begin{pmatrix} a_{11} & a_{12} & a_{13} \\ a_{21} & a_{22} & a_{23} \\ a_{31} & a_{32} & a_{33} \end{pmatrix} \begin{pmatrix} V_a \\ V_b \\ V_c \end{pmatrix}$$ [Formula 1]

The index value calculator 163 calculates an index value on the basis of a ratio between the corrected signal values ($V_a'$, $V_b'$, $V_c'$). The same method for calculating an index value as in the related-art example can be employed.

The water content calculator 164 converts the index value calculated by the index value calculator 163 into a water content by referring to a calibration curve 166 which was prepared in advance, and outputs information of the water content.

Figure 2:
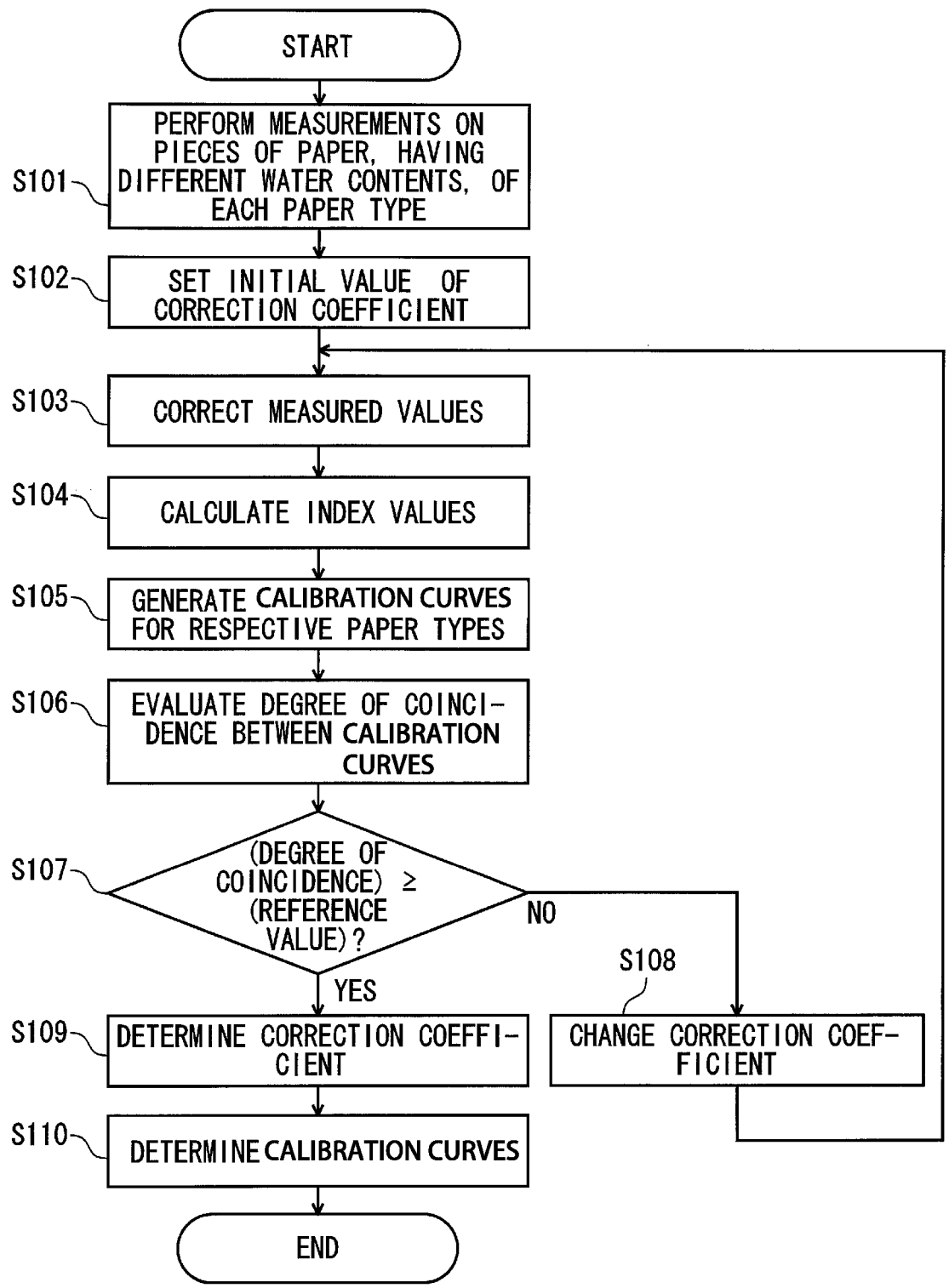
FIG. 2 is a flowchart showing a process for determining correction coefficient and calibration curve.

Next, a process for determining the correction coefficient 165 and the calibration curve 166 will be described with reference to a flowchart of FIG. 2. This process is executed on the manufacturer side before shipment of the infrared water content measuring apparatus 10 and, principle, need not be executed by a user. This allows the user to perform a high-accuracy measurement by making manipulations that are similar to manipulations to be made in the related-art example.

First, at step S101, plural types (products) of paper are prepared and pieces of paper, having different water contents, of each type are measured by the infrared water content measuring apparatus 10, whereby sets of uncorrected signal values ($V_a$, $V_b$, $V_c$) corresponding to intensities of the radiation beams having the respective wavelengths are acquired. It is assumed that correct water contents have been measured in advance using an electronic balance or the like.

To determine correction coefficient 165, its initial value is set at step S102. The initial value may be a base matrix of 3×3 given by Formula 2, which is equivalent to not performing correction.

$$\begin{pmatrix} 1 & 0 & 0 \\ 0 & 1 & 0 \\ 0 & 0 & 1 \end{pmatrix}$$ [Formula 2]

At step S103, the measured signal values ($V_a$, $V_b$, $V_c$) are corrected for each paper type using the thus-set correction coefficients. This can be done according to Formula 1. At step S104, an index value is calculated for each combination of a paper type and a water content on the basis of a ratio between the corrected signal values ($V_a'$, $V_b'$, $V_c'$).

Figure 3A:
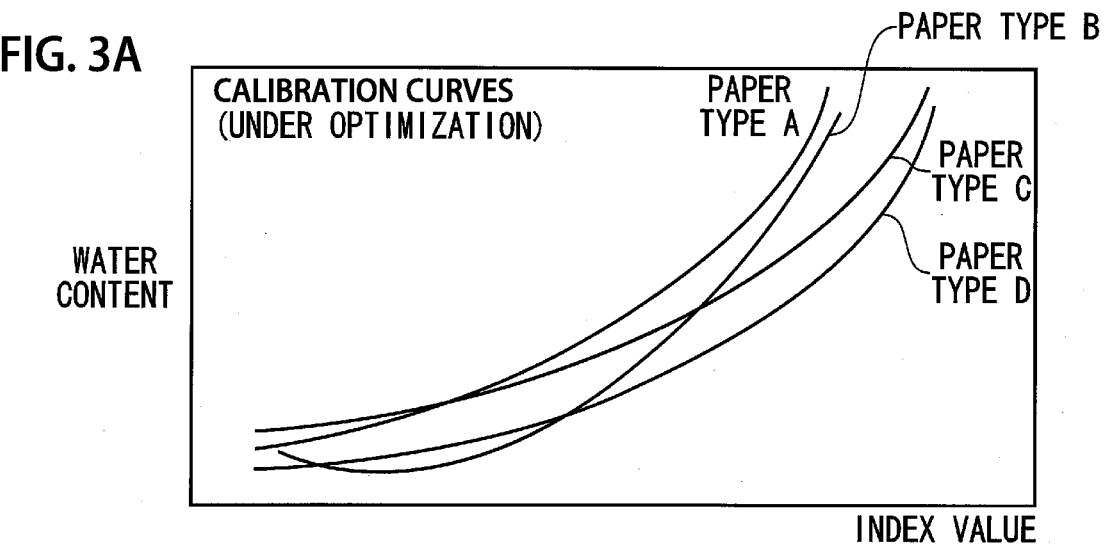
FIGS. 3A, 3B and 3C show calibration curves.

At step S105, a calibration curve is generated for each paper type using the index values calculated for the respective water contents. FIG. 3(a) shows calibration curves generated for a paper type A, a paper type B, a paper type C and a paper type D. FIG. 3(a) shows a state that the correction coefficient is its initial value and the calibration curves greatly vary. In this state, the apparatus is not suitable for practical use because different calibration curves need to be prepared for respective paper types.

At step S106, the degree of coincidence between the calibration curves is evaluated. For example, the degree of coincidence may be evaluated by determining one approximate curve by a multiple regression analysis and calculating the sum of errors between the approximate curve and each calibration curve.

If the evaluation result is that the degree of coincidence is lower than a reference value (S107: no), the correction coefficient is changed at step S108. An algorithm for changing the correction coefficient may be an arbitrary method such as a neighborhood search method or a Monte Carlo method. Steps S103-S107 are executed again using the new correction coefficient.

Figure 3B:
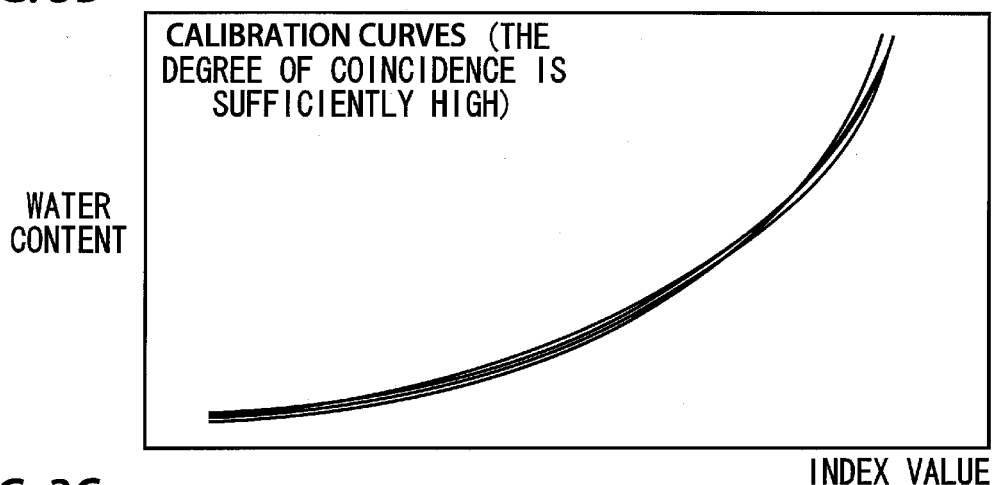

If the evaluation result is that the degree of coincidence is higher than or equal to the reference value (S107: yes), at step S109 the current correction coefficient is employed as final one. FIG. 3(b) shows a state that the degree of coincidence between the calibration curves has exceeded the reference value.

Figure 3C:
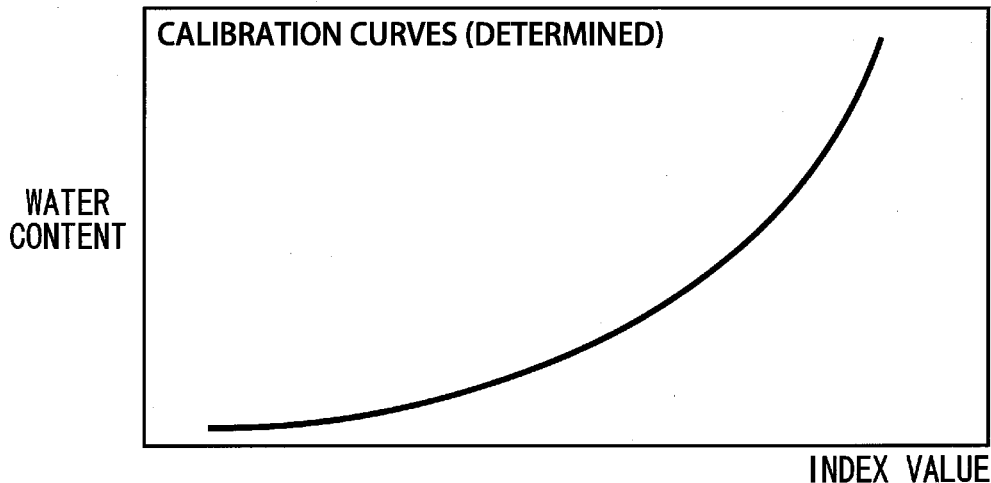

At step S110, a calibration curve to be used for actual measurements is determined which may be an approximate curve obtained by performing a multiple regression analysis on the calibration curves of the respective paper types obtained using the determined correction coefficient. FIG. 3(c) shows a calibration curve calculated on the basis of calibration curves of the respective paper types obtained using determined correction coefficient. The determination of the calibration curve 166 means that it is no longer necessary to use calibration curves for the respective paper types.

The correction coefficient 165 and the calibration curve 166 determined according to the above procedure are stored in a storage area provided in the processing unit 160.

Figure 4:
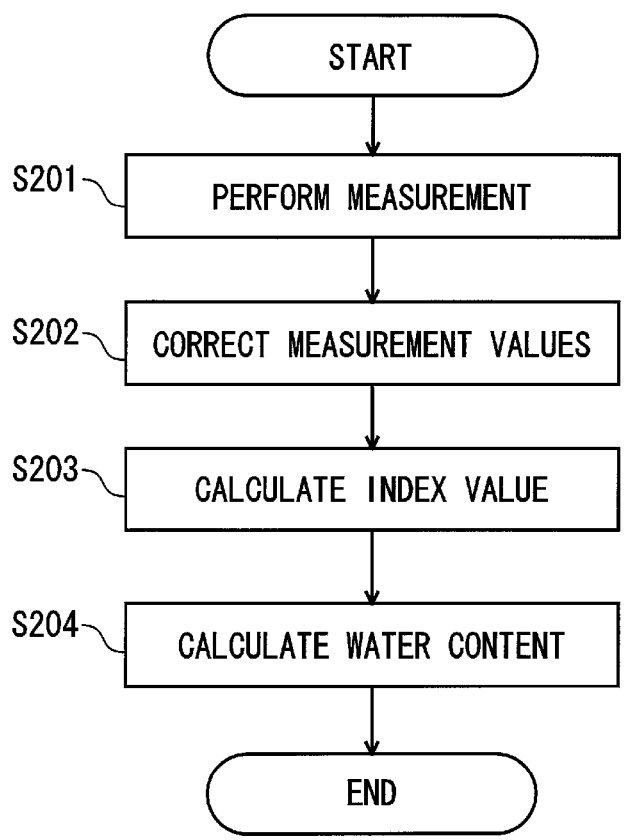
FIG. 4 is a flowchart showing a water content measuring process which is executed by the infrared water content measuring apparatus

Next, a water content measuring process which is executed by the infrared water content measuring apparatus 10 will be described below with reference to a flowchart of FIG. 4. It is assumed that the correction coefficient 165 and the calibration curve 166 have already been determined by the process of FIG. 2 and are stored in the storage area provided in the processing unit 160.

First, at step S201, a measurement process is executed in which radiation that is a mixture of radiation beams having the respective wavelengths is emitted from the LED unit 110 and applied to paper 700, resulting radiation is detected by the radiation receiver 150, and signal values corresponding to the respective wavelengths are obtained by the frequency discriminator 152. It is desirable that the measurement process be executed plural times. In this case, the filter section 161 of the processing unit 160 averages measurement results.

At step S202, the measurement value corrector 162 of the processing unit 160 corrects the measurement result by referring to the correction coefficient 165. At step S203, the index value calculator 163 calculates an index value on the basis of a corrected measurement result. At step S204, the water content calculator 164 converts the index value into a water content by referring to the calibration curve 166.

As described above, the infrared water content measuring apparatus 10 according to the embodiment can produce a measurement result with high accuracy even using radiation beams that do not have spectrum with extremely narrow half-value widths, because a measurement result is corrected using the correction coefficient 165 which can correct for mutual influences between radiation beams having the respective wavelengths.

Figure 5:
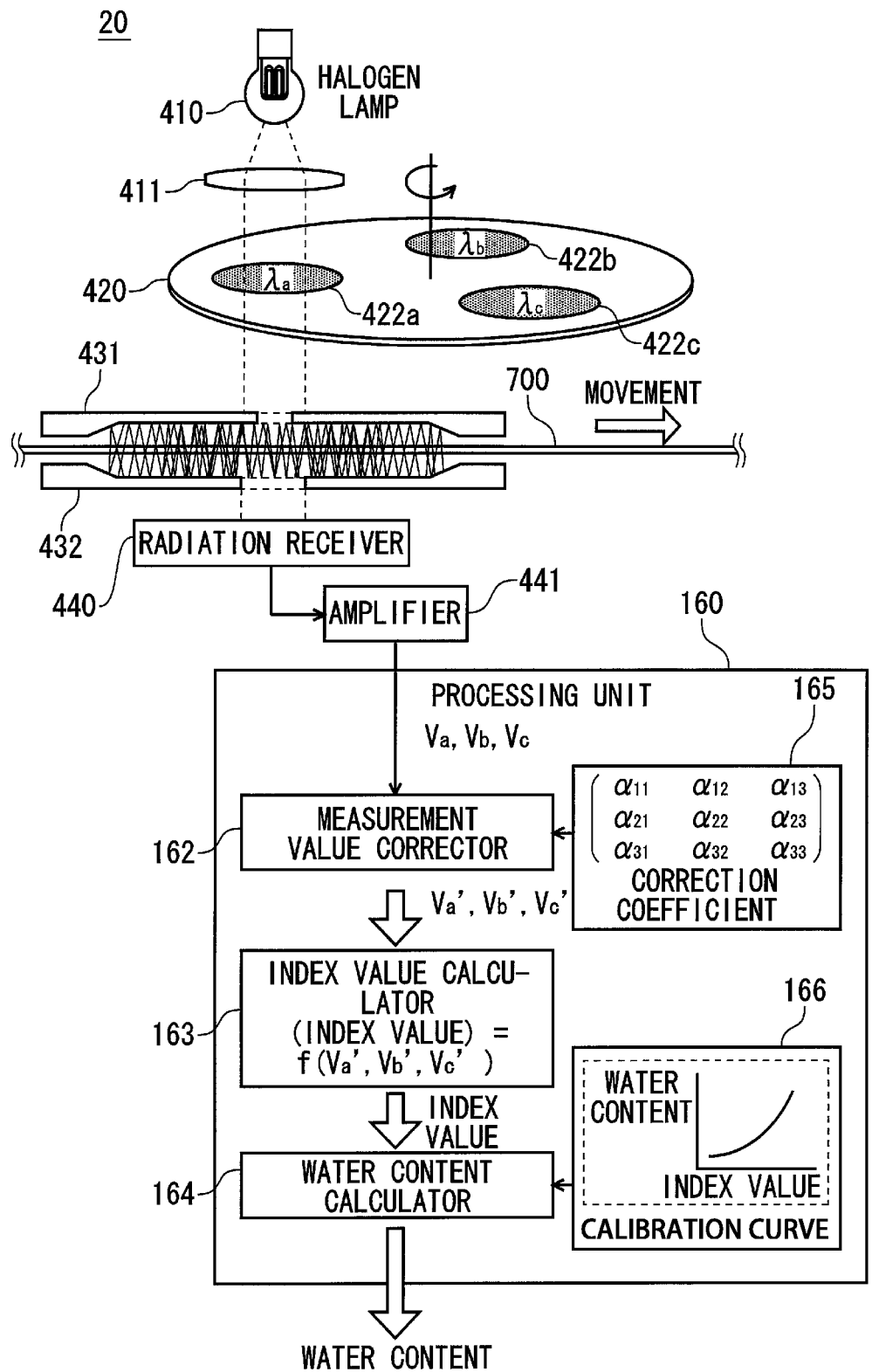
FIG. 5 is a block diagram showing another configuration of an infrared water content measuring apparatus according to the embodiment.
Figure 6:
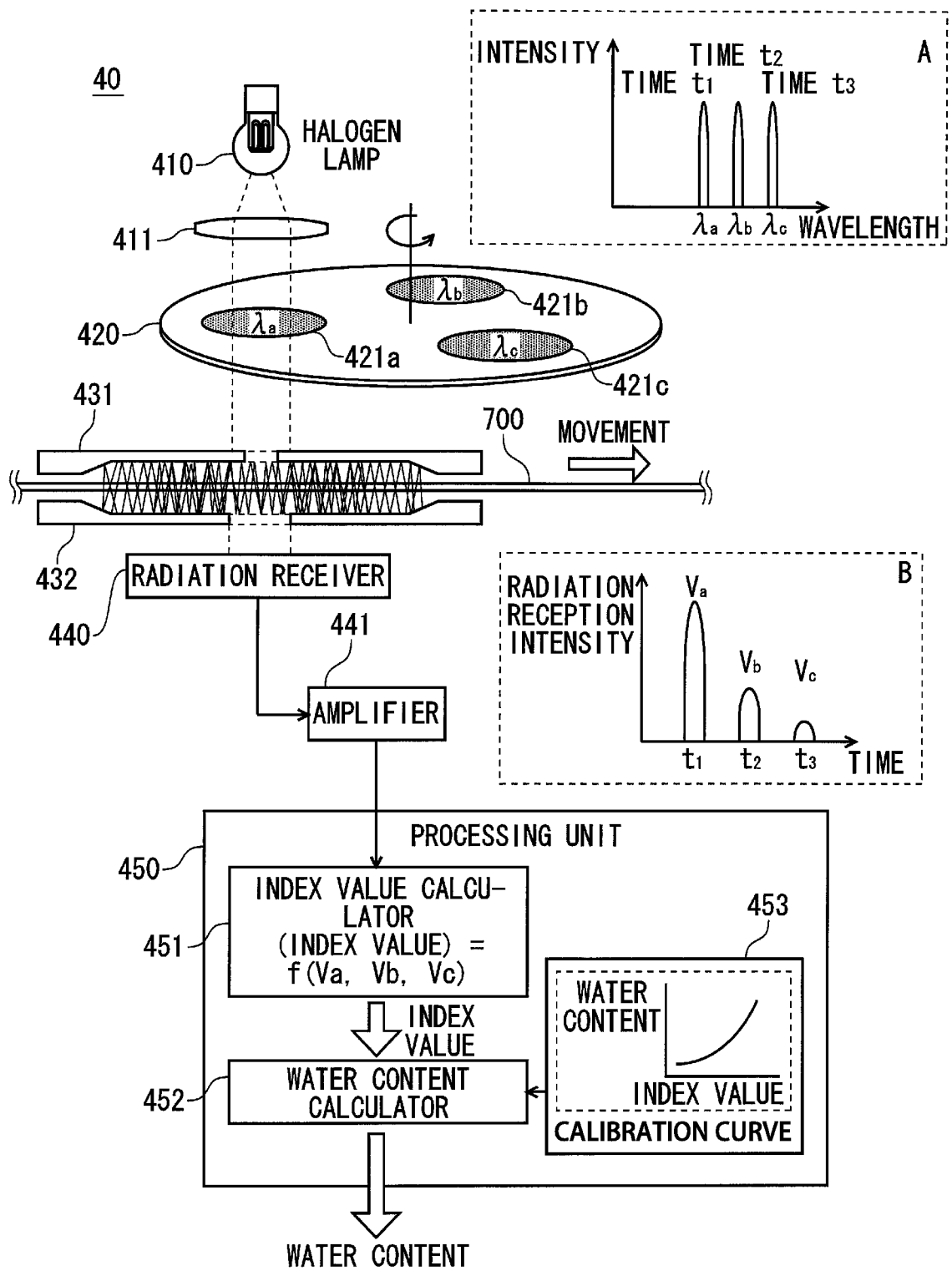
FIG. 6 is a block diagram showing the configuration of an infrared water content measuring apparatus according to a related art.
Figure 7:
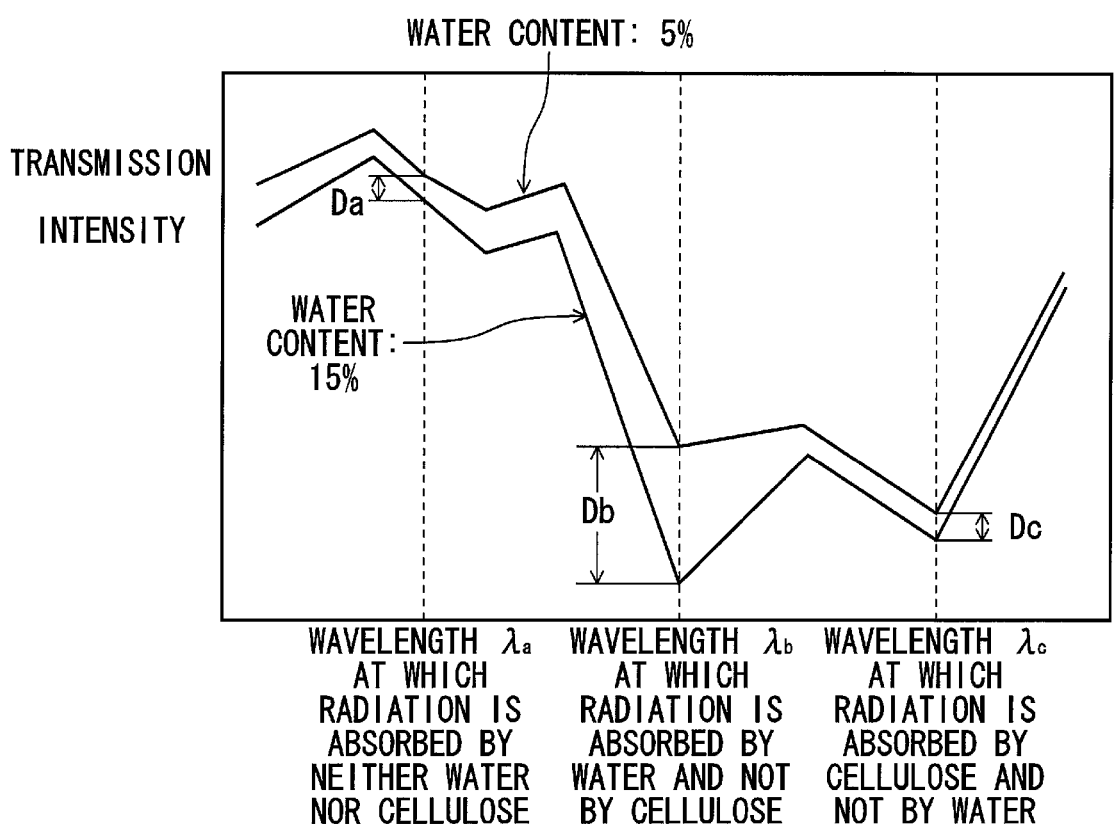
FIG. 7 is a graph showing the absorption characteristics at each wavelength in a case of the paper with the water content of 5% and in a case of the same paper with the water content of 15%.

Whereas in the above embodiment the LED unit 110 is used as a radiation source, the invention can also be applied to a case that the halogen lamp 410 is employed as a radiation source as in the related-art example. Furthermore, an LD (laser diode) or the like can also be used as a radiation source. FIG. 5 is a block diagram showing the configuration of an infrared water content measuring apparatus 20 to which the invention is applied and which employs the halogen lamp 410. Blocks having the same blocks in the related-art example are given by the same reference numerals as the latter and will be described only briefly.

In the infrared water content measuring apparatus 20 which employs the halogen lamp 410, radiation emitted from the halogen lamp 410 is guided, via the projection lens 411, to band-pass filters 422 which are mounted on the filter wheel 420.

Each of the band-pass filters 422 mounted on the filter wheel 420 is not required to produce radiation having a spectrum with an extremely narrow half-value width. This makes it possible to reduce the degree of radiation attenuation and hence to prevent size increase of the halogen lamp 410 even in the case of enabling measurement of even paper types having large basis weights.

Radiation that has passed through the band-pass filter 422 is applied to paper 700 as a measurement target which is interposed between the top reflector 431 and the bottom reflector 432. Radiation that is output through the exit hole of the bottom reflector 432 is detected by the radiation receiver 440 and a resulting detection signal is amplified by the amplifier 441. No frequency discriminator is used because the halogen lamp 410 is not suitable for electrical modulation.

The amplified detection signal is input to the processing unit 160 and corrected by the measurement value corrector 162 using the correction coefficient 165. The filter section 161 may be provided to average results of plural measurements. Then, an index value is calculated by the index value calculator 163 on the basis of a ratio between detection signal values corresponding to the respective wavelengths. The index value is converted into a water content by the water content calculator 164 by referring to the calibration curve 166. The correction coefficient 165 and the calibration curve 166 are ones that were determined according to the above-described process.

Although the embodiment of the invention has been described above, the invention is not limited to it. For example, the number of reference radiation beams may be increased in which case four or more radiation beams having different wavelengths are applied to paper 700 as a measurement target material. Another configuration is possible in which a measurement is performed by applying two radiation beams having different wavelengths that do not include the wavelength that is absorbed by cellulose to the measurement target material and a cellulose content measured by another measuring apparatus such as a basis weight meter is used. In these cases, the order of the correction coefficient is set according to the number of wavelengths. Where four or five wavelengths are used, the correction coefficient may be set to a square matrix of 4×4 or 5×5. Where two wavelengths are used, the correction coefficient may be set to a square matrix of 2×2.

In addition, the order of the correction coefficient is not necessarily the same as the number of wavelengths. Although the description of the embodiment was given as a case where the correction was performed with the square matrix of 3×3 since the LEDs were used for all the three radiation sources and the wavelength regions thereof were partially overlapped with each other, it is also possible to perform the correction with a square matrix of m×m with respect to the number n of wavelengths (m is an integer that is smaller than n). An index value is calculated based on relative intensities of radiation beams having n wavelengths after the correction with the square matrix of m×m. Although it is considered in this case that a degree of improvement effect is lower than that in a case of using the correction coefficient as the square matrix of n×n, it is expected that the improvement effect itself by the correction can be achieved.

In addition, it is also possible to use a non-square matrix that is obtained by omitting a row or a column, correction for which is not necessary, from the square matrix of n×n with respect to the number n of wavelengths.

For example, it is possible to use such a non-square matrix in a case where a laser diode (LD) can be employed as one of the three radiation sources. Since wavelength regions of the LEDs are overlapped with each other, it is necessary to correct the mutual influence of the wavelengths. In addition, in a case where the wavelengths of the LEDs increase up to the wavelength of the LD, it is necessary to correct an influence of the wavelength of the LD with respect to detected intensity of the radiation beams having the wavelengths of the LEDs. In contrast, since a half width of the LD is extremely narrow in general, there is no influence of the wavelengths of the other LEDs. Accordingly, there is a case where it is necessary to correct the detected intensity of the radiation beams having the wavelengths of the LEDs while it is not necessary to correct the detected intensity of the radiation beams having the wavelength of the LD. In such a case, it is possible to use a non-square matrix, which is obtained by omitting a row or a column corresponding to the correction on the detected intensity of the radiation beams having the wavelength of the LD, as a correction coefficient. In addition, when the wavelength of the LD is set to the wavelength $\lambda a$ that is not absorbed by either moisture or cellulose, an output directly corresponds to transmittance of the measurement target material, and there is an advantage in that the apparatus and the measurement values can be easily managed.

The mutual correction makes it unnecessary to manage the wavelengths of radiation beams to be irradiated strictly, which in turn enables use of inexpensive LEDs in wavelength bands for other purposes such as a communication purpose or in long wavelengths in a wavelength band with excellent transmittance. Although the above description is directed to the transmission-type infrared water content measuring apparatus, the invention can also be applied to reflection-type infrared water content measuring apparatus or water content measuring apparatus using microwaves.

By modifying the method for calculating an index value from a measurement result or changing the conversion target physical quantity of the calibration curve, the invention can also be applied to an apparatus for measuring a surface property, a transmission scattering property, a basis weight, a coating thickness, an ash content, or a like property of paper.

The present application is based on Japanese Patent Application (JP-A-2012-073652) filed on Mar. 28, 2012, the content of which is incorporated herein as a reference.

REFERENCE SIGNS LIST

10: infrared water content measurement apparatus
20: infrared water content measurement apparatus 40: infrared water content measurement apparatus
110: LED unit
120: LED drive
121: modulator
130: tube reflector
131: diffusion sheet
141: top reflector
142: bottom reflector
143: glass window
150: radiation receiver
151: amplifier
152: frequency discriminator
160: processing unit
161: filter section
162: measurement value corrector
163: index value calculator
164: water content calculator
165: correction coefficient
166: calibration curve
410: halogen lamp
411: projection lens
420: filter wheel
421: band-pass filter
421: respective band-pass filter
431: top reflector
432: bottom reflector
440: radiation receiver
441: amplifier
450: processing unit
451: index value calculator
452: water content calculator
453: calibration curve

The invention claimed is:

1. A material property measuring apparatus comprising:
a radiation source irradiator configured to irradiate a measurement target material with radiation beams having n different wavelengths;
a detector configured to detect intensities of radiation beams having the respective wavelengths after the irradiation of the measurement target material; and
a processing unit configured to correct the detected intensity of the radiation beam having at least a part of the respective wavelengths using a correction coefficient in which rows and columns are respectively represented by a matrix of an order of n or less, and to calculate an index value indicating a property of the measurement target material on the basis of relative intensities of the radiation beams having the respective wavelengths after the correction, wherein
the processing unit converts the calculated index value into a property value by referring to a calibration curve which correlates the index value with the property value, after the calculation of the index value,
the correction coefficient is determined so that the degree of coincidence between calibration curves for a plurality of kinds of the measurement target material satisfies a certain criterion, and
the calibration curve to be used for actual measurement is one calibration curve which is common to the plurality of kinds of the measurement target material.

2. A material property measuring apparatus comprising:
a radiation source irradiator configured to irradiate a measurement target material with radiation beams having n different wavelengths;
a detector configured to detect intensities of radiation beams having the respective wavelengths after the irradiation of the measurement target material; and
a processing unit configured to correct the detected intensities of the radiation beams having the respective wavelengths using a correction coefficient which is represented by a square matrix of an order of n, and to calculate an index value indicating a property of the measurement target material on the basis of relative intensities of the radiation beams having the respective wavelengths after the correction, wherein
the processing unit converts the calculated index value into a property value by referring to a calibration curve which correlates the index value with the property value, after the calculation of the index value,
the correction coefficient is determined so that the degree of coincidence between calibration curves for a plurality of kinds of the measurement target material satisfies a certain criterion, and
the calibration curve to be used for actual measurement is one calibration curve which is common to the plurality of kinds of the measurement target material.

3. The material property measuring apparatus according to claim 1, wherein the radiation source irradiator comprises n LEDs (Light Emitting Diodes) which emit radiation beams having the respective wavelengths, respectively.

4. The material property measuring apparatus according to claim 3, wherein
the radiation source irradiator drives the n LEDs while modulating them at different frequencies; and
the detector comprises a frequency discriminator configured to detect a signal having a particular frequency from a frequency-modulated signal.

5. The material property measuring apparatus according to claim 3, wherein the radiation source irradiator reflects and diffuses the radiation beams emitted from the n LEDs and irradiates the measurement target material with the radiation beams simultaneously.

6. The material property measuring apparatus according to claim 1, wherein
the measurement target material is paper;
the property is a water content; and
the radiation beams having the n different wavelengths has three or more wavelengths, and include a radiation beam having such a wavelength as to be absorbed by water, a radiation beam having such a wavelength as to be absorbed by cellulose, and a radiation beam having such a wavelength as not to tend to be absorbed by water or cellulose.

7. The material property measuring apparatus according to claim 1, wherein the radiation source irradiator includes a tube reflector or a light pipe which orders spatial uniformity of the radiation beams having the respective wavelengths.

8. The material property measuring apparatus according to claim 2, wherein the radiation source irradiator comprises n LEDs (Light Emitting Diodes) which emit radiation beams having the respective wavelengths, respectively.

9. The material property measuring apparatus according to claim 8, wherein
the radiation source irradiator drives the n LEDs while modulating them at different frequencies; and
the detector comprises a frequency discriminator configured to detect a signal having a particular frequency from a frequency-modulated signal.

10. The material property measuring apparatus according to claim 8, wherein the radiation source irradiator reflects and diffuses the radiation beams emitted from the n LEDs and irradiates the measurement target material with the radiation beams simultaneously.

11. The material property measuring apparatus according to claim 2, wherein
   the measurement target material is paper;
   the property is a water content; and
   the radiation beams having the n different wavelengths has three or more wavelengths, and include a radiation beam having such a wavelength as to be absorbed by water, a radiation beam having such a wavelength as to be absorbed by cellulose, and a radiation beam having such a wavelength as not to tend to be absorbed by water or cellulose.

12. The material property measuring apparatus according to claim 2, wherein the radiation source irradiator includes a tube reflector or a light pipe which orders spatial uniformity of the radiation beams having the respective wavelengths.

* * * * *